United States Patent [19]

Bucalo

[11] Patent Number: 5,267,572
[45] Date of Patent: Dec. 7, 1993

[54] BIOPSY INSTRUMENT WITH TISSUE SPECIMEN RETAINING AND RETRIEVAL DEVICE

[76] Inventor: Brian D. Bucalo, 1010 South Ocean Blvd., Pompano, Fla. 33062

[21] Appl. No.: 946,923

[22] Filed: Sep. 17, 1992

Related U.S. Application Data

[62] Division of Ser. No. 616,220, Nov. 20, 1990, Pat. No. 5,148,813.

[51] Int. Cl.$^5$ ............................................... A61B 10/00
[52] U.S. Cl. ................................................... 128/754
[58] Field of Search ............... 128/749, 751, 753, 754; 606/167, 170, 171, 184

[56] References Cited

U.S. PATENT DOCUMENTS

| | | | |
|---|---|---|---|
| 3,001,522 | 9/1961 | Silverman | 128/754 |
| 3,175,554 | 3/1965 | Stewart | 128/754 |
| 3,929,123 | 12/1975 | Jamshidi | 128/754 |
| 3,990,451 | 11/1976 | Gibbs | 128/754 |
| 4,651,752 | 3/1987 | Fuerst | 128/754 |
| 4,682,606 | 7/1987 | DeCaprio | 128/754 |
| 4,785,826 | 11/1988 | Ward | 128/754 |
| 4,881,550 | 11/1989 | Kothe | 128/751 |
| 4,926,877 | 5/1990 | Bookwalter | 128/754 |

FOREIGN PATENT DOCUMENTS

3430910 3/1985 Fed. Rep. of Germany ...... 128/754

Primary Examiner—Max Hindenburg
Attorney, Agent, or Firm—Steinberg & Raskin

[57] ABSTRACT

A biopsy instrument combines a tissue penetrating device including a cutting member with a specimen retaining and retrieval device. The specimen retaining and retrieval device is detachably connected to the tissue penetrating device and operates, after the cutting member has penetrated into tissue, to separate a specimen of tissue enclosed by the cutting member from surrounding tissue. The specimen retaining and retrieval device can then, while retaining the specimen therein, be detached from the tissue penetrating device and transferred to a desired location such as a vial containing preservative solution for the specimen.

5 Claims, 8 Drawing Sheets

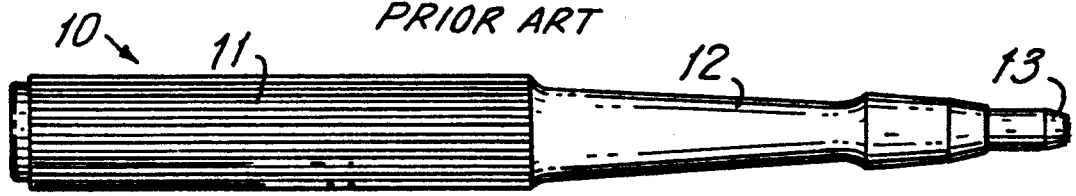
FIG. 1
PRIOR ART
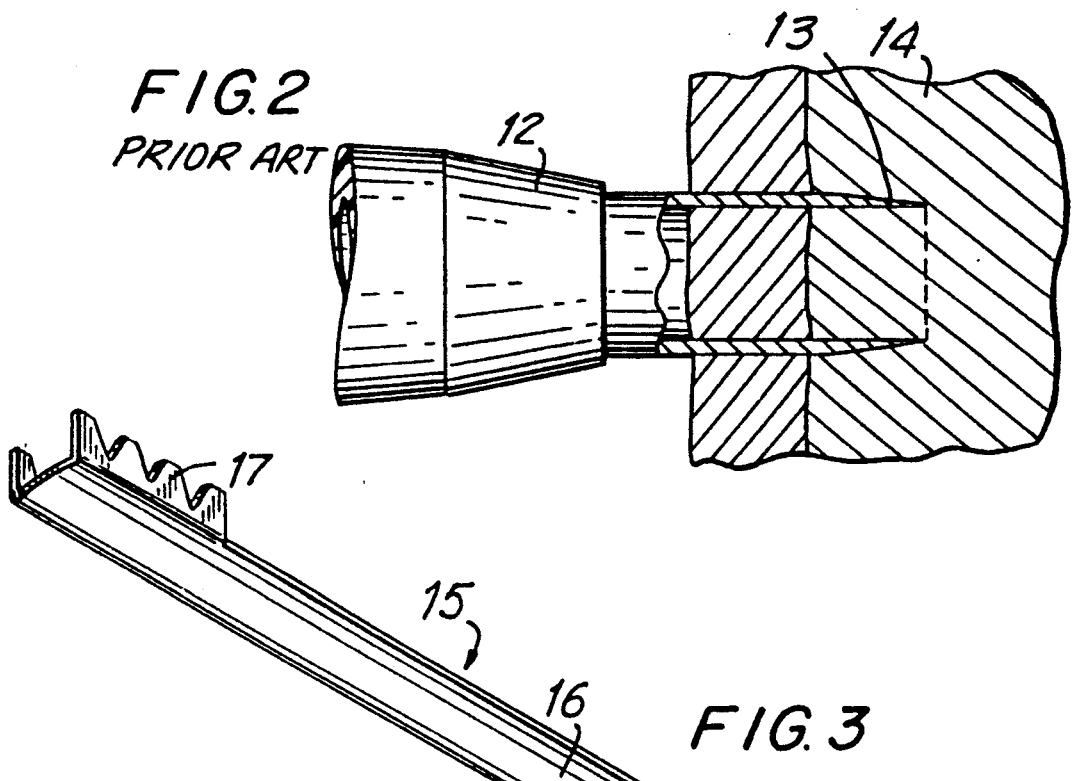
FIG. 2
PRIOR ART
FIG. 3
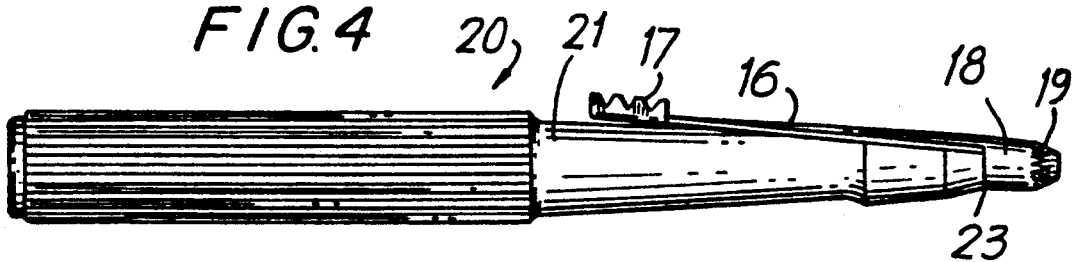
FIG. 4

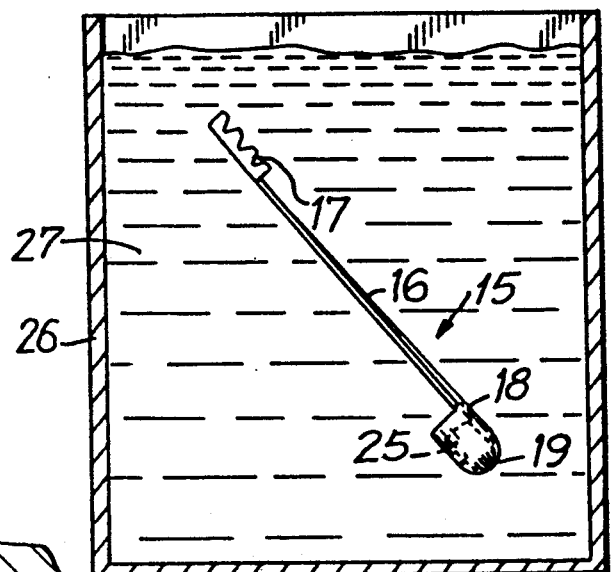
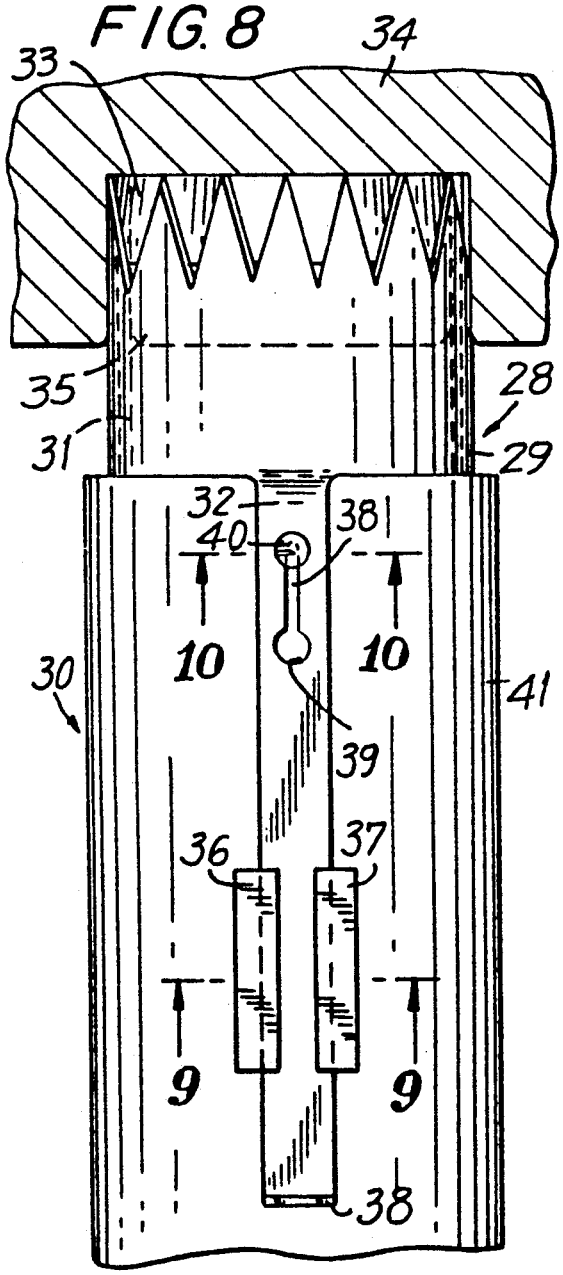
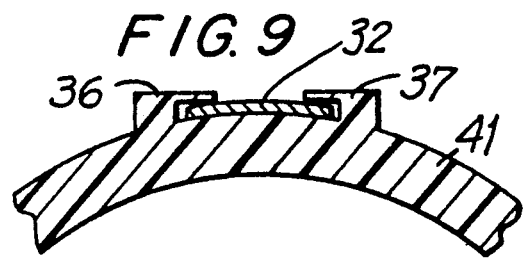
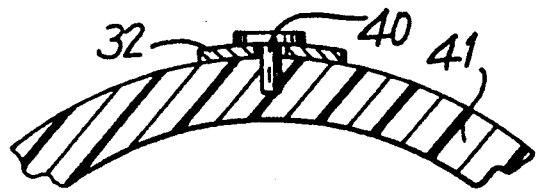

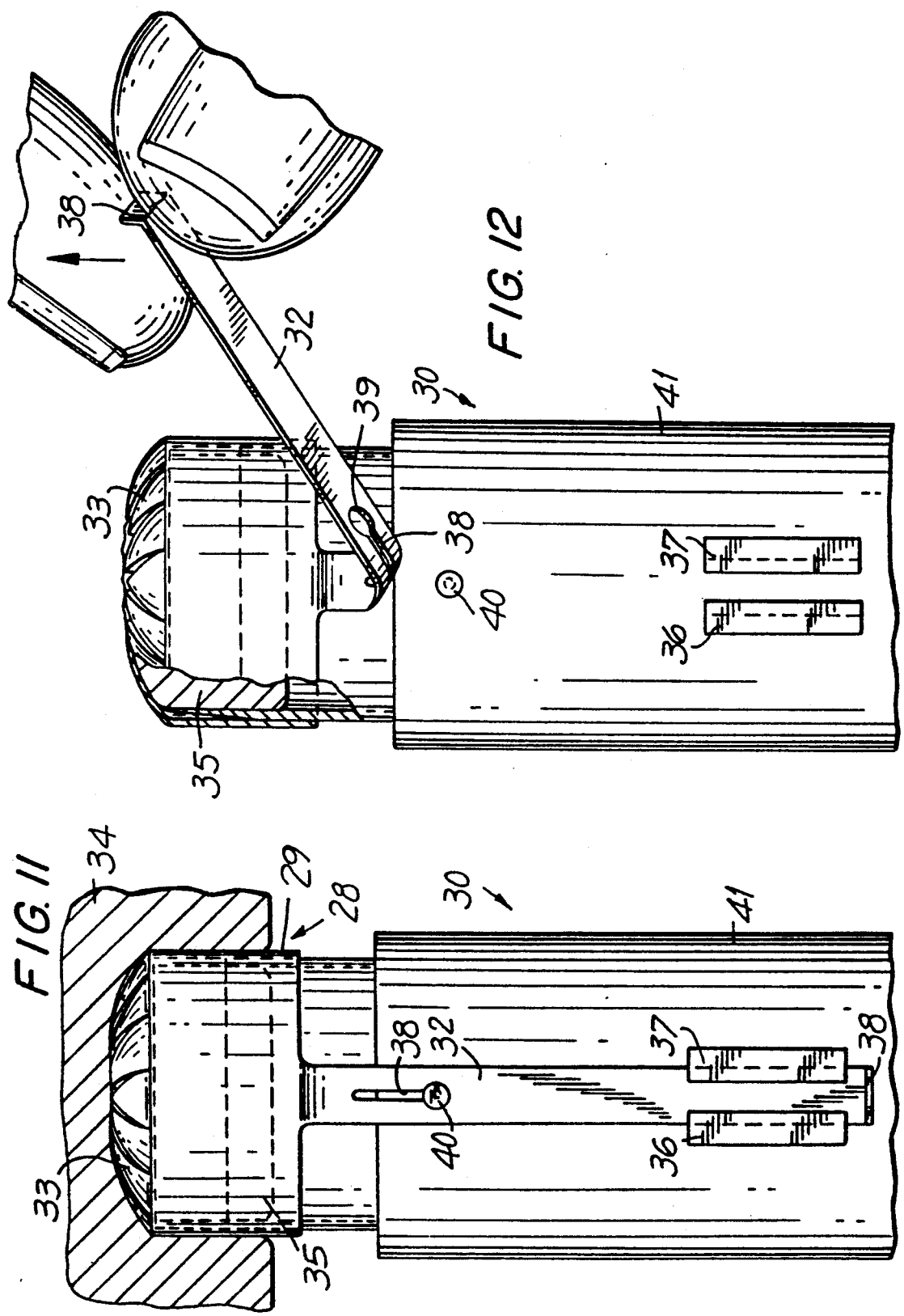

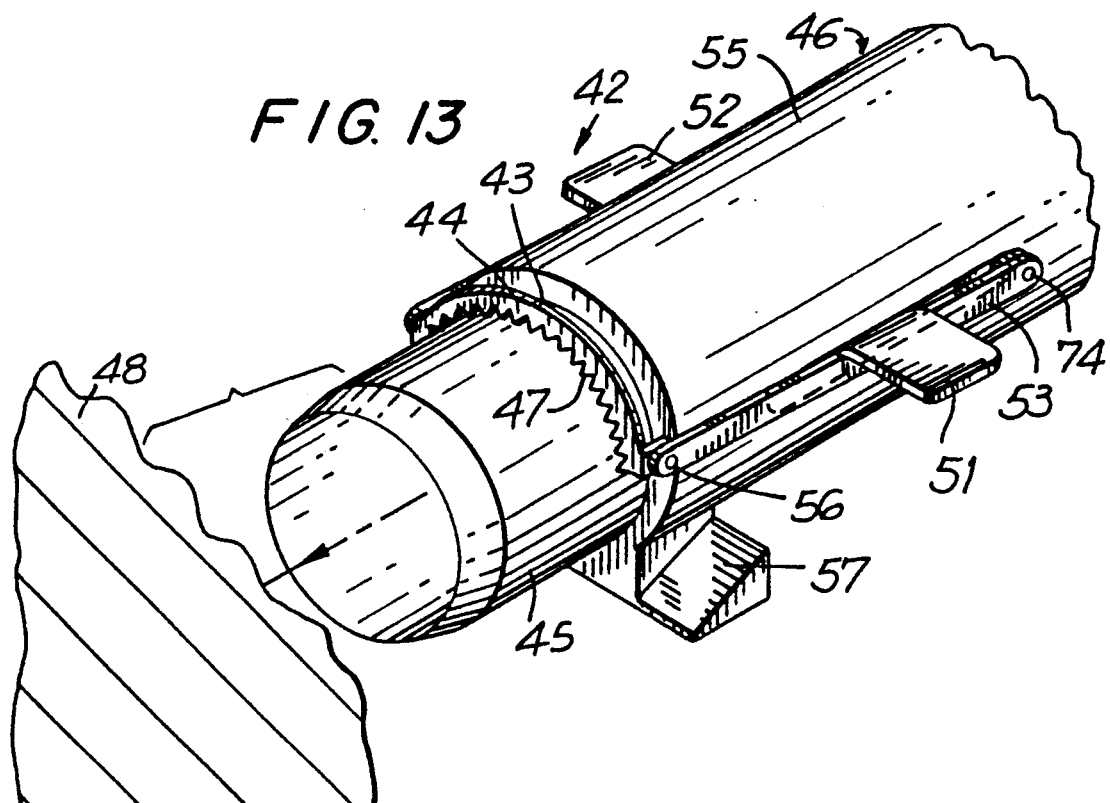
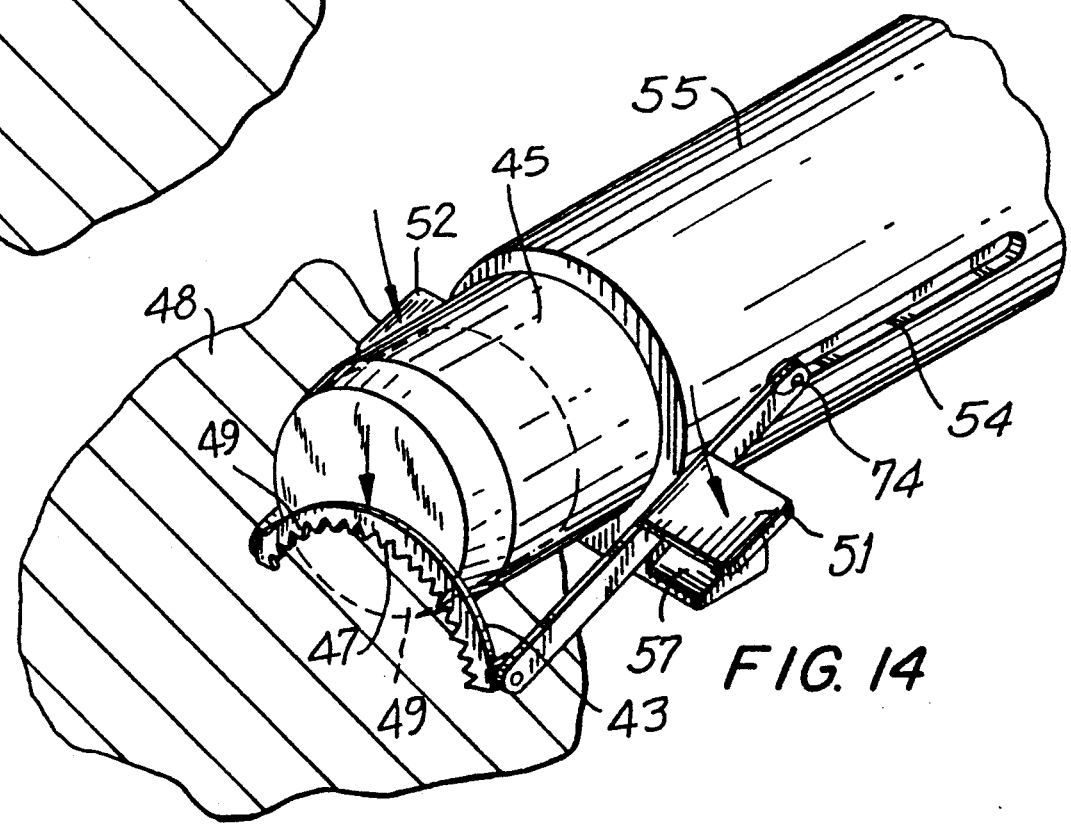

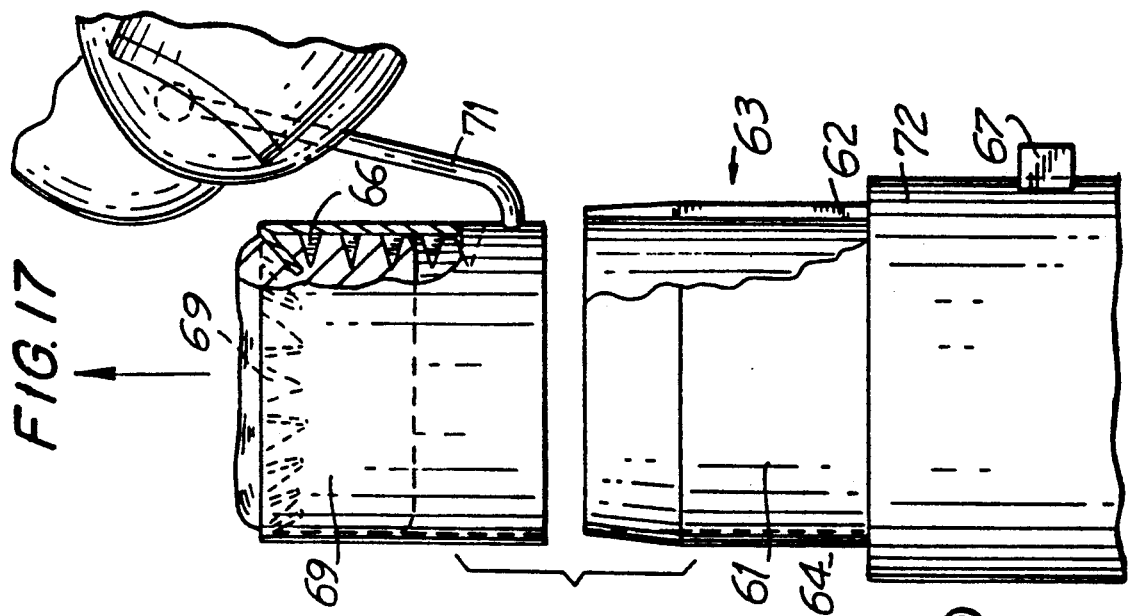
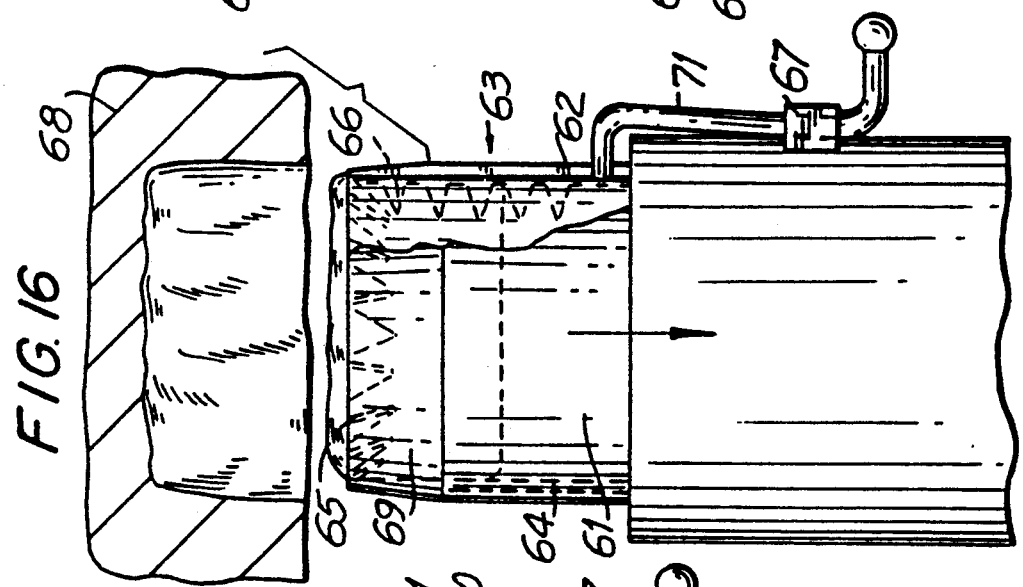
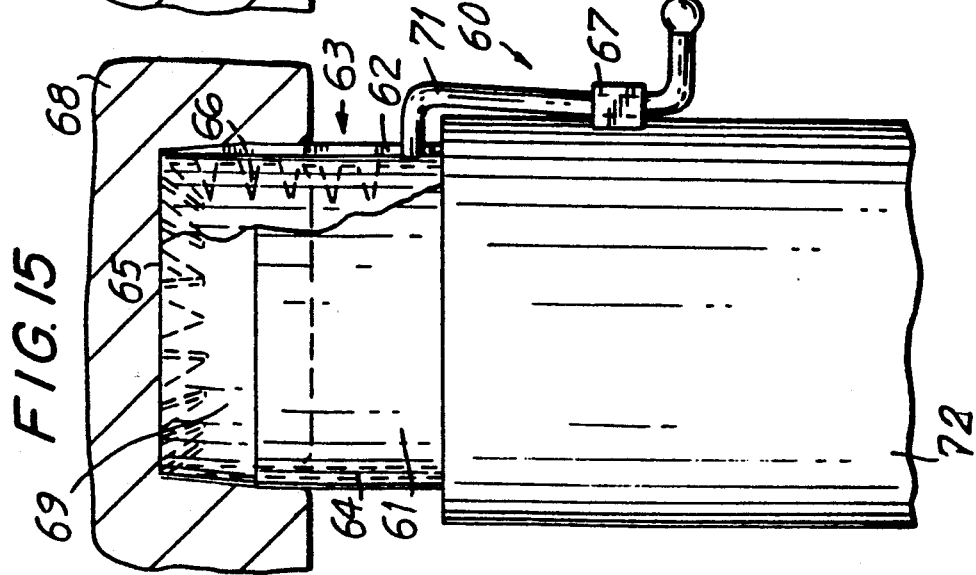

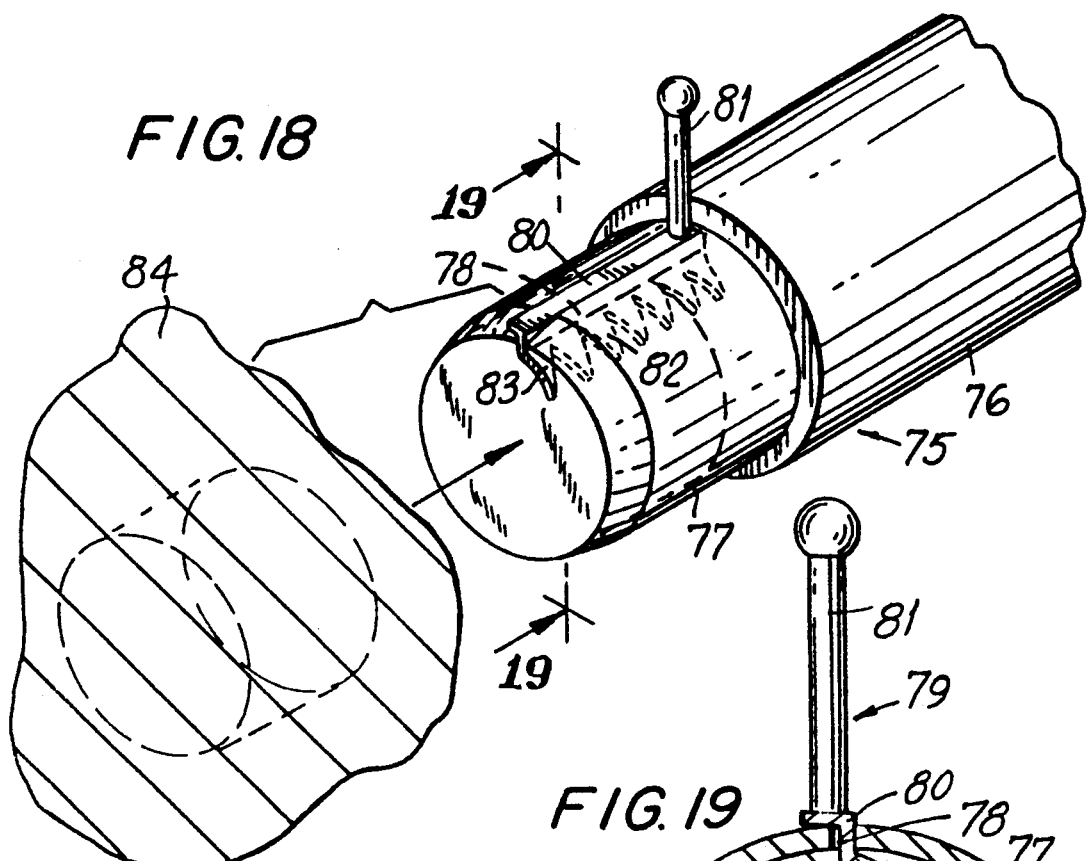
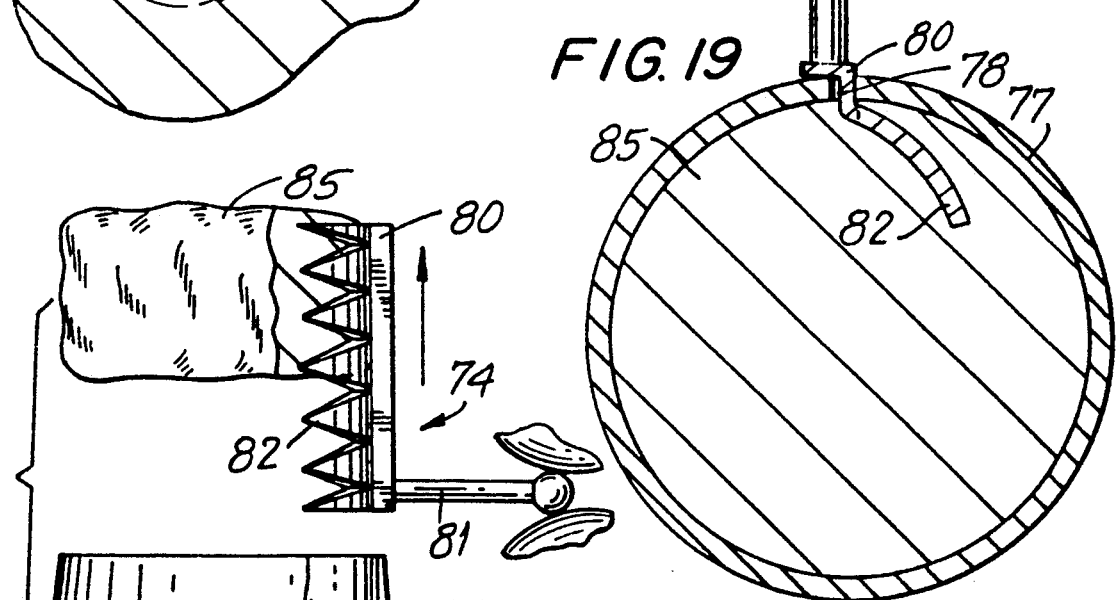
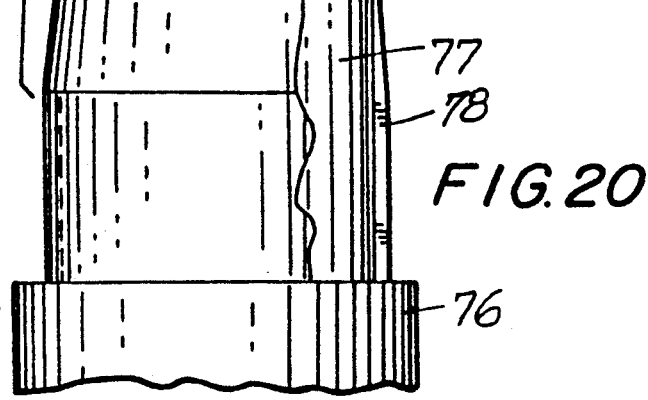

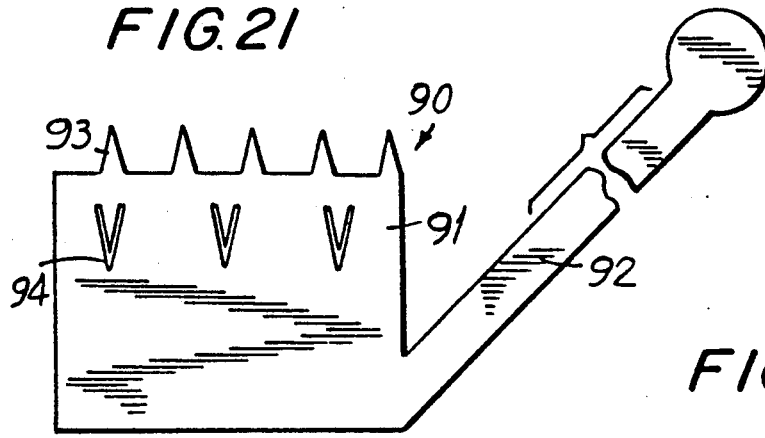
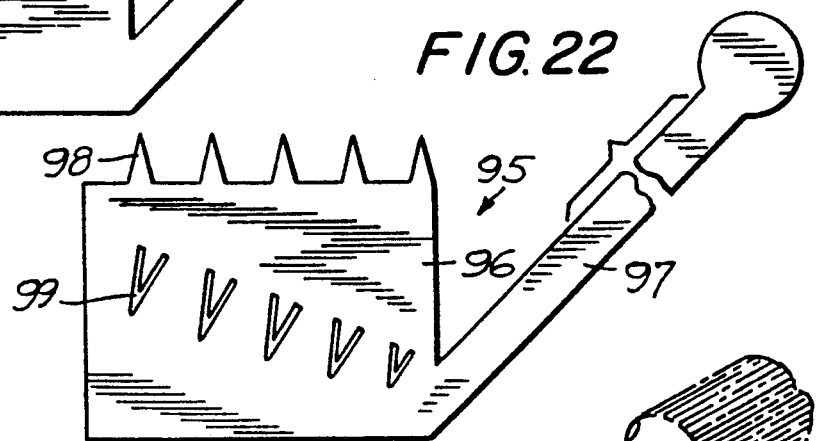
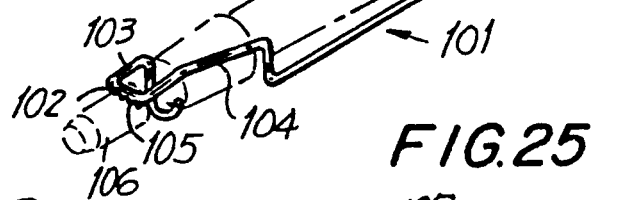
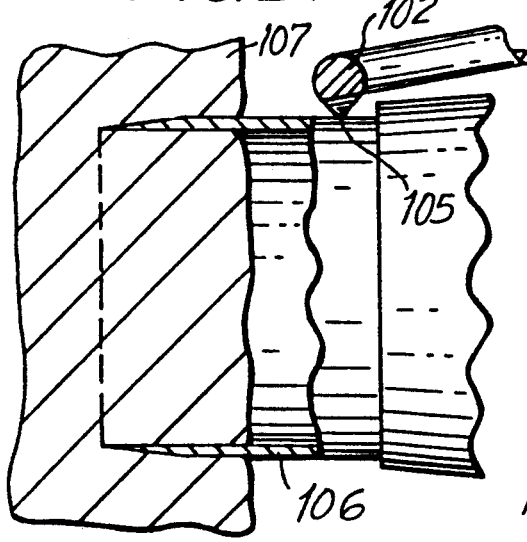
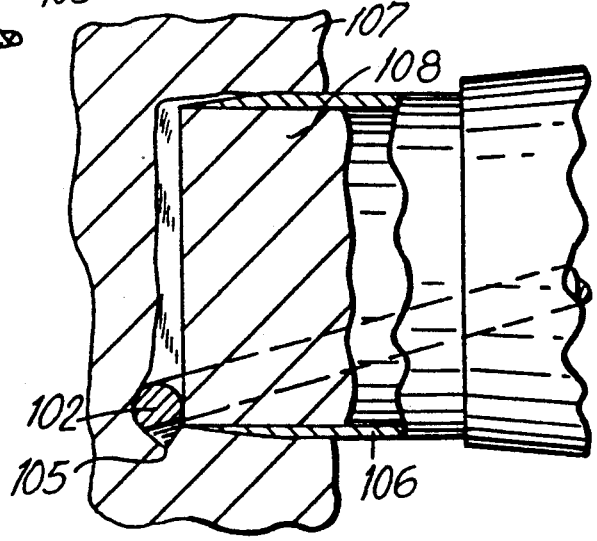

BIOPSY INSTRUMENT WITH TISSUE SPECIMEN RETAINING AND RETRIEVAL DEVICE

This is a division, of application Ser. No. 07/616,220, filed Nov. 20, 1990, now U.S. Pat. No. 5,148,813.

BACKGROUND OF THE INVENTION

The present invention relates to biopsy instruments used in collecting specimens of tissue from the skin or internal organs for analysis. The invention particularly relates to skin punch biopsy devices which are conventionally used to bore cylindrical channels in the skin by rotating a tubular cutting sleeve to advance the sleeve into tissue.

A serious problem which has occurred with conventional punch type biopsy instruments is that these instruments are incapable of separating the tissue specimen from the surrounding tissue once the rotational cutting action has been completed. Almost invariably, as the biopsy instrument has been withdrawn, the tissue specimen remains attached to the body at the uncut portion of its base and must then be lifted with a needle point or tweezers and the attached base portion excised with a scalpel blade. This secondary operation is not only tedious and time consuming but also requires additional equipment in the form of a scalpel and unnecessarily places medical personnel at risk for such infectious diseases as hepatitis and AIDS through accidental needle punctures, scalpel cuts, or blood splashes. Also, this secondary removal operation is very difficult to perform on agitated human patients or on unwieldy animals.

An additional problem which arises with conventional skin punch biopsy instruments concerns the fact that the collected biopsy specimens are normally placed in a vial containing preservative solution. Thus, specimens which are small in size are often difficult to find and retrieve, especially if the preservative solution has been darkened with blood or other body fluids from the specimen.

One attempt to solve some of the above-mentioned problems is found in U.S. Pat. No. 4,785,826, issued to Ward. This patent discloses a biopsy needle having a first hollow member with a second elongated hollow member fitted within the first hollow member. The second member has a flexible end portion included pointed segments which are normally opened to receive a tissue specimen, and which can be closed by moving the inner member axially with respect to the outer member (by means of twisting one with respect to the other). The tapered segments are deformed by a shoulder formed on the inner surface of the outer member, thereby being bent inwardly to cut and capture a tissue specimen.

SUMMARY OF THE INVENTION

Accordingly, one object of the present invention is to provide a biopsy instrument which efficiently removes tissue specimens and which provides efficient contact with and retrieval from preservative solutions.

Another object of the present invention is to provide a new and improved biopsy instrument which has located along its outside surface a removable, tissue specimen retaining and retrieval means incorporating a series of barbs which engage the specimen and remove it from the surrounding tissue when the biopsy instrument is withdrawn.

Still another object of the present invention is to provide a biopsy instrument which will rapidly and easily lift the biopsy specimen from the surrounding tissue and eliminate the need for manual lifting and excision of the biopsy tissue specimen, thereby saving time, equipment costs, and preventing the exposure of health care personnel to the hazards of blood borne infections, as well as reducing the time required for removal of a tissue specimen from agitated patients or unwieldy animals.

Yet another object of the present invention is to provide a tissue specimen retaining device comprising a combination of a specimen retaining means and a handle to provide greater flexibility in connection with transporting the biopsy tissue specimen to the preservative solution providing for efficient contact with the preservative, and in retrieving the tissue specimen therefrom.

A further object of the present invention is to provide a tissue specimen retaining device which may easily be retrofitted for use on existing biopsy punch instruments.

A still further object of the present invention is to provide a biopsy instrument that may be operated to collect a tissue specimen while requiring utilization of only one hand of the operator.

These and other objects are attained in accordance with the present invention by providing an improved biopsy instrument which comprises a detachable tissue specimen retaining and retrieval device which device utilizes a plurality of barbs to sever a tissue specimen from a volume of tissue into which the biopsy instrument has bored, and which device also has a handle which is detachable from the rest of the biopsy instrument such that the device holding the severed tissue specimen can easily be transferred to and removed from a preservative solution. The tissue retaining and retrieval device, although generally rotatable relative to the tissue penetrating means of the conventional biopsy instrument, contains means for preventing this relative rotation.

In one preferred embodiment of the invention the tissue specimen retaining and retrieval device comprises a handle detachably connecting it to a conventional punch type biopsy instrument, a sleeve integral with the handle and located so as to surround the cylindrical cutting member of the biopsy instrument as it bores into tissue, and barbs integral with an end of the sleeve and exerting a radially inward pressure on the cylindrical cutting member. The handle can be advanced axially relative to the cylindrical cutting member whereupon the barbs sever a specimen from the tissue and retain it within the sleeve member. The specimen retaining and retrieval device comprising the handle, the sleeves, and the barbs can then be detached, containing the severed tissue specimen, from the rest of the biopsy instrument for transferral to a vial containing preservative solution.

In another preferred embodiment of the invention the tissue specimen retaining device comprises a band mounted on the outside surface of the cylindrical cutting member of the biopsy instrument and having a serrated front edge comprising a plurality of barbs aligned side by side to form an arc impinging on a portion of the outside surface of the cylindrical cutting member and downwardly. After the cylindrical cutting member has bored into a volume of tissue, by pushing forwardly on a pair of arms respectively mounted on two shafts mounted lengthwise in slots on the cutting member with each shaft attached to an opposite end of the barbs the band can be advanced forwardly relative to the cylindrical cutting member and then pivoted downwardly to sever a tissue specimen whereupon the retaining and retrieval device can be detached from the biopsy instrument and transferred to a preservative solution.

Another preferred embodiment of the present invention comprises a simpler variation of the specimen retaining and retrieval device of the invention comprising a band mounted on the outside of the cylindrical cutting member of the biopsy instrument. In this embodiment the band comprises a substantially straight front edge member integral at its respective ends with two handle members which function to enable the band to be mounted on the biopsy instrument such that the front edge can contact the outside surface of the tubular cutting member. The handle members also provide sufficient tension to the front edge member such that, when the front edge member is pushed past the front of tubular cutting member after the cutting member has bored into tissue, the front edge member, which can have a knife edge or a serrated toothed edge, snaps down to sever a tissue specimen. The band can then be detached from the rest of the biopsy instrument while retaining the tissue specimen for further handling.

In still another preferred embodiment the cutting member of the biopsy instrument has a longitudinal slot which runs for its entire length whereby the cutting member forms an incomplete cylinder. In this embodiment the specimen retaining device has a sleeve member concentric with and abutting the interior surface of the biopsy instrument cutting member. The sleeve member has a first set of flexible barbs located on its forward edge and oriented so as to point axially in a rearward direction. A second optional set of flexible barbs are located in parallel with each other and spaced apart longitudinally on the interior surface of the sleeve member and oriented so as to point in the circumferential direction of the sleeve. The specimen retaining device has a removal member or handle integral with the sleeve member which projects through the slot in the cutting member of the biopsy instrument. An adhesive element holds the removal member to the handle of the biopsy instrument. As the cutting member of the biopsy instrument bores into a volume of tissue, part of the tissue enters the sleeve member of the specimen retaining device whereby it bends, but does not engage, the first set of flexible barbs to pin them against the inside surface of the sleeve. Rotation of the sleeve causes the second set of barbs to engage the tissue. Thereupon the cutting member is withdrawn from the tissue causing the first set of flexible barbs to engage and sever the tissue such that a specimen is retained within the sleeve of the retaining device. Then the removal member or handle is pulled away from the biopsy instrument whereupon it and the sleeve containing the severed tissue specimen can be transferred to a vial containing preservative solution.

Another embodiment of the invention having many aspects similar to the embodiment last previously mentioned comprises the cutting member of the biopsy instrument having a longitudinal slot running along its entire length and the specimen retaining device having a sleeve member concentric with and abutting the interior surface of the biopsy instrument cutting member. In this embodiment the sleeve member has a first set of flexible barbs located on its forward edge and oriented so as to point rearward in an axial direction. A second set of flexible barbs is located on the inside surface of the sleeve member, the second set of barbs also being oriented to point rearwardly in an axial direction and being aligned substantially in parallel with each other to point in a direction substantially parallel with the longitudinal axis of the sleeve, with the second set of barbs situated substantially in parallel with each other along the inner surface of the sleeve at a substantially constant distance from the forward edge. The specimen retaining device has a removal member or handle integral with the sleeve member which projects through the slot in the cutting member of the biopsy instrument. An adhesive element holds the removal member to the handle of the biopsy instrument. As the cutting member of the biopsy instrument bores into a volume of tissue, part of the tissue enters the sleeve member of the specimen retaining device where it presses both the first and second sets of flexible barbs to pin them against the inside surface of the sleeve member. Thereupon the cutting member is withdrawn from the tissue causing the first and second sets of barbs to engage and sever the tissue such that a specimen is retained within the sleeve of the retaining device. Then the removal member or handle is detached from the biopsy instrument and the sleeve containing the severed tissue specimen can be transferred to a vial containing preservative solution.

Still another embodiment of the invention is identical to the embodiment just mentioned except that the second set of barbs are aligned so as to point at an acute angle with the longitudinal axis of the sleeve.

In yet another preferred embodiment of the invention the cutting biopsy instrument has a longitudinal slot which runs for its entire length whereby the cutting member forms an incomplete cylinder. A shaft having a handle attached thereto is mounted on the cutting member above the slot. Inside the cutting member is a set of flexible barbs integrally connected to the shaft through the slot in the cutting member. These flexible barbs are oriented to point in the circumferential direction of the cutting member. As the cutting member of the biopsy instrument bores into tissue, the set of flexible barbs is pressed against the inner surface of the cutting instrument. A knife edge can be provided on the front edge of the barb closest to the front edge of the cutting member to facilitate moving the cutting member with the barbs therein into the tissue. After the cutting member has been advanced for a desired distance into the tissue, it can be rotated such that the barbs engage the tissue within the cutting member. Rearward movement of the biopsy instrument then causes a specimen of tissue to detach whereupon it is held by the barbs within the cutting member. The handle can then be moved through the slot to detach it and the barbs having the tissue specimen attached thereto from the biopsy instrument. The retaining and retrieval device with the specimen therein can then be transferred to a vial containing preservative solution.

BRIEF DESCRIPTION OF THE DRAWINGS

A more complete appreciation of the present invention and many of the attendant advantages thereof will be readily understood by reference to the following detailed description when considered in connection with the accompanying drawings in which:

FIG. 1 is an elevational view of a prior art biopsy instrument;

FIG. 2 is an enlarged sectional view of a portion of the instrument shown in FIG. 1;

FIG. 3 is a perspective view of a preferred embodiment of the specimen retaining and retrieval device for the biopsy instrument of the present invention;

FIG. 4 is a perspective view of a preferred embodiment of a biopsy instrument comprising the specimen retaining and retrieval device of FIG. 3;

FIG. 7 is an elevational view of a vial containing preservative solution with the specimen retaining and retrieval device of the present invention containing a tissue specimen and being immersed in a vial containing preservative solution;

FIG. 8 is a sectional view showing the details of another preferred embodiment of the biopsy instrument of the present invention;

FIG. 9 is a cross-sectional view taken along the lines 9—9 of FIG. 8;

FIG. 10 is a cross-sectional view taken along the lines 10—10 of FIG. 8;

FIG. 11 shows the biopsy instrument of FIG. 8 with the specimen retaining means therein having been pushed forwardly axially to grasp a tissue specimen:

FIG. 12 is a sectional view illustrating the detachment of the specimen retaining device from the biopsy instrument of FIG. 8;

FIG. 13 is a perspective view of another preferred embodiment of the specimen retaining device for the biopsy instrument of the present invention;

FIG. 14 shows the specimen retaining device of FIG. 13 in engagement with a tissue specimen;

FIG. 15 is a longitudinal sectional view of another preferred embodiment of the biopsy instrument of the invention.

FIG. 16 is a longitudinal sectional view of the biopsy instrument of FIG. 15 with a tissue specimen retained within the retaining and retrieval device therein.

FIG. 17 is a longitudinal sectional view showing the detachment of the specimen retaining device of FIGS. 15 and 16 from the biopsy instrument thereof.

FIG. 18 is a perspective view, partially in section, of another preferred embodiment of the biopsy instrument of the invention.

FIG. 19 is a sectional view of the embodiment of FIG. 18 showing the biopsy instrument holding a specimen of tissue.

FIG. 20 is an elevational view showing the biopsy instrument of FIG. 18 with the specimen retaining and retrieval device detached therefrom.

FIG. 21 is an elevational view of a manufacturing blank for another preferred embodiment of a retaining and retrieval device for the biopsy instrument of the invention.

FIG. 22 is an elevational view of a manufacturing blank for another preferred embodiment of a retaining and retrieval device for the biopsy instrument of the invention.

FIG. 23 is a sectional perspective view of another preferred embodiment of the biopsy instrument of the present invention.

FIG. 24 is a sectional view of the biopsy instrument of FIG. 23 entering an area of tissue.

FIG. 25 is a sectional view of the biopsy instrument of FIG. 23 wherein the retaining and retrieval device has functioned to sever and grasp a tissue specimen.

DESCRIPTION OF THE PREFERRED EMBODIMENTS

Figure 5:
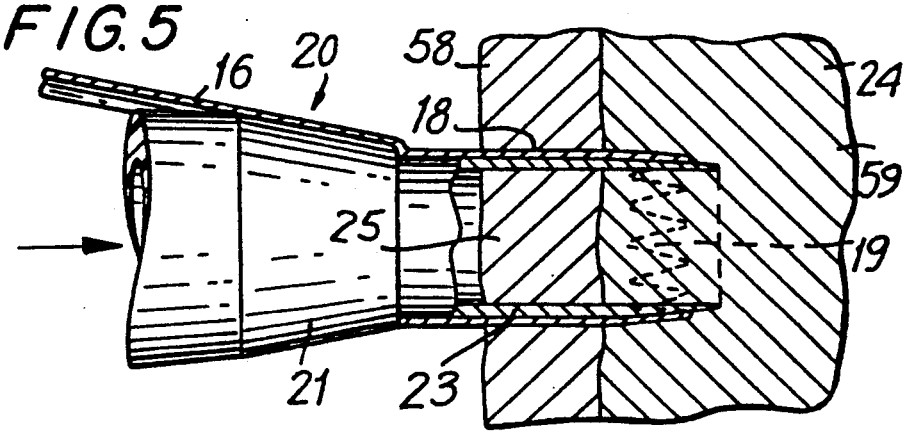
FIG. 5 is an enlarged sectional view of a portion of the biopsy instrument of FIG. 4, with the instrument being shown having penetrated into tissue, for a collection of a specimen therefrom.

Referring now to the drawings wherein like reference characters designate identical or corresponding parts throughout the several views, and more particularly to FIG. 1, a prior art biopsy instrument, generally designated 10, comprises a handle having a cylindrical section 11 and a tapering section 12 integrally attached at one end thereto. Mounted in the other end of section 12 is a cylindrical metallic cutting member 13 which bores a cylindrical channel into tissue to enclose a specimen therein.

FIG. 2 is an expanded sectional view of the biopsy instrument 10 of FIG. 1. As shown therein, cutting member 13 has penetrated into tissue 14 to surround a section of tissue therein. However, as indicated heretofore, after the biopsy instrument 10 is retracted from the tissue 14, the tissue specimen must then be lifted with a needle point or tweezers and its base portion excised with a scalpel blade.

FIG. 3 shows a preferred embodiment of the specimen retaining and retrieval device of the present invention wherein the device, generally designated 15, comprises a flexible metal strip 16 with a series of ridges 17 at one thereof to facilitate moving the strip which functions as a handle for the retaining and retrieval device, and a cylindrical sheath 18 integral with the other end of the strip 16 and adapted to fit around the cylindrical cutting member of a biopsy instrument. A plurality of flexible barbs 19 are integral with the end of cylindrical sheath 18 opposite the flexible metal strip 16 and are deformed so as to apply a radially directed inward pressure on the exterior of the cylindrical cutting member of a biopsy instrument.

FIG. 4 shows the retaining device 15 of FIG. 3 functioning as a detachable part of a biopsy instrument generally labelled 20 as shown therein, the flexible metal strip 16 rests on the handle 21 of the biopsy instrument 20, and the sheath 18 surrounds the cylindrical cutting member 23 of biopsy instrument 10 with the barbs 19 attached to a distal end of the cylindrical sheath 18.

Again referring to FIG. 4, an important feature of flexible strip 16 is that it allows, simply by applying finger pressure thereon, for the prevention of relative rotation between the specimen retaining and retrieval device 15 and the tissue penetrating means comprising handle 21 and cylindrical cutting member 23 during use of the biopsy instrument. Such control of the relative rotation between the specimen retaining and retrieval device and the tissue penetrating means is common to all of the embodiments of the invention disclosed herein.

FIGS. 5, 6, 6A, 6B and 7 show various stages in the retaining and preservation for retrieval of a tissue specimen by the biopsy instrument 20 of FIG. 4. As shown in FIG. 5, the biopsy instrument 20 has penetrated tissue 24 (comprising a plurality of tissue layers 58, 59) such that a tissue section 25 is surrounded by cylindrical cutting member 23.

Figure 6:
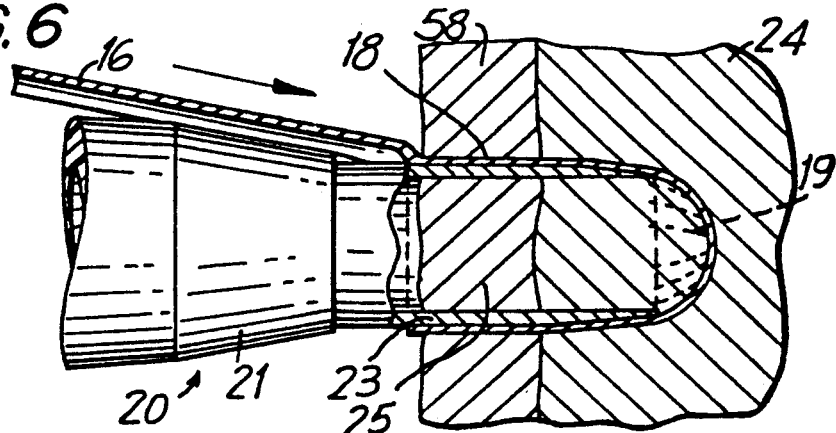
FIG. 6 shows the biopsy instrument of FIG. 5 with the specimen retaining and retrieval device having been operated to grasp a tissue specimen.

FIG. 6 shows the sheath member 18 of the retaining device 15 having been moved forward axially relative to the biopsy instrument cutting member 23 such that it penetrates further into the tissue 24 than in FIG. 5 and such that its barbs 19 flex inward to grasp and sever tissue specimen 25.

Figure 6A:
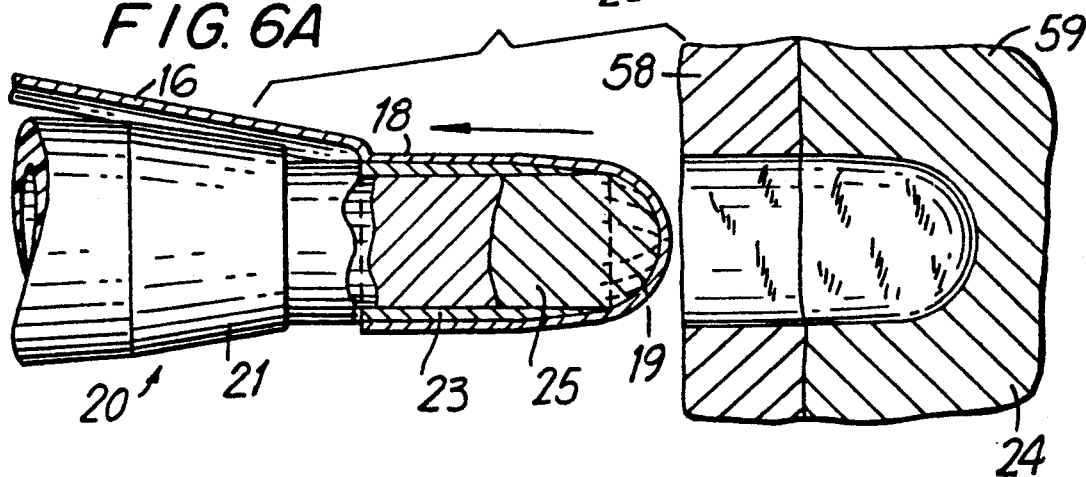
FIG. 6A shows the biopsy instrument of FIG. 6 withdrawn from the tissue.

FIG. 6A shows the biopsy instrument 20 having been withdrawn from tissue 24 such that tissue specimen 25 is retained therein.

Figure 6B:
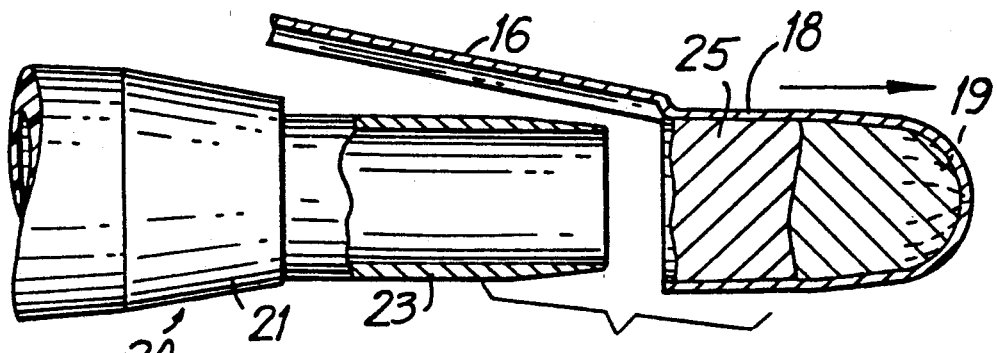
FIG. 6B shows the retaining and retrieval device with the specimen therein detached from the rest of the biopsy instrument.

FIG. 6B shows the detachment of retaining device 15 from biopsy instrument 20 with the retention of tissue specimen 25 in the retaining device 15. This detachment is produced by pulling strip handle 16 outward from the handle 21.

FIG. 7 shows the retaining device 15 immersed in preservative liquid 27 contained in a vial 26. As shown therein, the tissue specimen 25 is securely held by the cylindrical sheath 18 and collapsed barbs 19, and can easily be retrieved from the preservative liquid 27 by grasping the strip handle 16.

FIG. 8 is a longitudinal sectional view showing another preferred embodiment of the biopsy instrument of the present invention. As shown therein, specimen retaining and retrieval device 28 comprises a cylindrical sheath member 29 concentric with and located on the outside surface of tubular cutting member 31 of biopsy instrument 30, relative to which the sheath member 29 is axially movable. Strip handle 32 is integrally connected with sheath member 29. Flexible barbs 33 form a part of specimen retaining device 28 and are deformed so as to apply radially directed inward pressure on the exterior surface of tubular cutting member 31. Cutting member 31 is shown penetrating tissue 34 such that it surrounds a portion 35 thereof. Guide members 36, 37 are located on the outside surface of instrument 30 and permit the axial movement of handle 32 with respect to biopsy instrument 30 while preventing relative rotational movement between handle 32 and instrument 30. The proximal end of handle 32 is bent to form a tab 38 which limits the forward travel of handle 32 because of the interference between tab 38 and guide members 36, 37. A hole 39 in handle 32 adjoins a slit 38 thereof. A pin 40 projects through slit 38 from cutting member holder 41 of biopsy instrument 30 and permits relative axial movement between handle 32 and instrument 30 while preventing relative rotational movement therebetween. The head of the pin holds handle 32 to the outside surface of holder 41.

FIG. 9 is a view of the biopsy instrument of FIG. 8 taken along the lines 9—9. As shown therein, the guide members 36, 37 are located symmetrically with respect to cutting member holder 41 of biopsy instrument 30.

FIG. 10 is a view of the biopsy instrument of FIG. 8 taken along the lines 10—10. As shown therein, pin 40 traverses slit 38 of handle 32 to enter cutting member holder 41.

In FIG. 11 the handle 32 has been moved forwardly relative to its position in FIG. 8 by a distance equivalent to the length of slit 38 thereby advancing the specimen retaining device 28 an equivalent distance into tissue 34. Flexible barbs 33, now unsupported by the cylindrical cutting member 23 of biopsy instrument 20, flex inward to grasp tissue specimen 35. Tab 38 abuts the end of guide elements 36, 37, thereby preventing any further axial movement of handle 32. Pin 40 is now centered over a hole 31.

FIG. 12 shows handle 32 being detached from biopsy instrument 20 by grasping tab 38 and pushing the handle 32 axially through the space between the guide members 36 distance and 37 and then pulling the pin 40 through the hole 38. The interference distance between guide members 36 and 37 and handle 32 is very small and the flexibility of handle 32 allows it to easily be displaced from between the guide members for this detachment. Specimen retaining device 28 containing tissue specimen 25 therein, which comprises handle 32, thereby detaches from holder 41 whereby it may then be placed in a vial of preservative solution.

FIG. 13 shows another preferred embodiment of the invention wherein a specimen retaining device generally designated 42 comprises a band 43 attached at each end by pins (only 56 shown) to shafts (only 53 shown) having a serrated edge 44 and resting on top of cutting member 45 of biopsy instrument 46. Barbs 47 are located along the serrated edge 44 of band 43.

FIG. 14 shows the specimen retaining device 42 of FIG. 13 wherein band 43 has been advanced forward and downward to thereby cause barbs 47 to engage tissue 48 and sever the tissue specimen 49 from the rest of the tissue 48. This result can be produced by pushing forward on arms 50, 51 respectively integral with shafts (only 53 shown) which are movable within slots (only 54 shown) in cutting member holder 55 of biopsy instrument 46. The shafts are pivotable about pivot pins (only 74 shown) such that the band 53 with its serrated edge can be moved downward to sever tissue 48 and retain tissue specimen 49 within tissue specimen retaining and retrieval device 42. Stop members (only 57 shown) limit the downward movement of band 53. The pivot 74 can be removed to detach specimen retaining and retrieval device from holder 55 such that device 34 and tissue specimen 49 can be transferred to a vial of preservative solution.

FIGS. 15-17 illustrate another preferred embodiment of the specimen retaining device of the present invention wherein, as shown in FIG. 15, a biopsy instrument generally designated 60 has a cylindrical cutting member 61 with a longitudinal slot 62 therein and extending from holder 72. A specimen retaining device generally designated 63 has a cylindrical member 64 which is concentric with and abuts the interior surface of cutting member 61. Flexible barbs 65 are located near or on the interior front edge surface of member 64 and are oriented such that they point rearwardly in an axial direction. Another set of flexible barbs 66 are located in a parallel array on the longitudinal interior surface of cylindrical member 64 and are oriented such that they point inwardly. A removal member or handle 71 is an integral part of specimen retaining device 63 and projects through the linear slot 62. An adhesive element 67 holds the removal member 71 in contact with the holder 72. In FIG. 15 the cutting member 61 is advanced into tissue 68, a portion 69 of which is held within the specimen retaining means 63 thereby deforming, but not engaging, the flexible barbs 65 against the inside of cylindrical member 64. If cutting member 61 is rotated in a direction opposite to its direction of rotation when boring into tissue, barbs 65 will engage tissue 68.

FIG. 16 shows the tissue retaining device 63 and biopsy instrument 60 of FIG. 15 with cutting member 61 withdrawn from tissue 68 whereby flexible barbs 65 and 66 engage tissue 68 causing tissue specimen 69 to be retained within the interior of specimen retaining device 63.

FIG. 17 shows the tissue retaining device 63 and biopsy instrument 60 of FIGS. 15 and 16 wherein removal member 71 has been pulled away from adhesive element 67 and holder 72, causing the specimen retaining device 63 containing tissue plug 69 to slide out of cutting member 61. The assembly of tissue retaining means 63 containing tissue specimen 69, and removal member 71 may then be placed in a vial of preservative solution for subsequent easy retrieval at a later date.

FIGS. 18-20 illustrate yet another preferred embodiment of the invention wherein a biopsy instrument, generally designated 75 comprises a holder 76 to which is attached a cylindrical cutting member 77. The cylindrical cutting member 77 has a longitudinal slot 78 therein. A specimen retaining and retrieval device, generally designated 79, comprises a member 80 having an L-shaped cross section with one leg of the L resting atop slot 78 of cylindrical cutting member 77 and the other leg of the L extending down through slot 78. The L shaped member has a length corresponding to that of slot 78 and has a handle 81 mounted thereon. Attached to the end of the leg of the L-shaped member 80 which protrudes down through slot 78 are a set of barbs 82. The barbs 82 are pressed against the inner circumferential surface of cutting member 77 as it bores into tissue 84 to collect a specimen 85 therefrom. The first barb 83 mounted at the front edge of L-shaped member 80 can be provided with a knife edge to facilitate its entering the tissue before the front edge of cutting member 77.

FIG. 19 shows cutting member 77 having been rotated such that the barbs 82 engage and hold tissue specimen 85.

FIG. 20 shows handle 81 having been grasped and moved forward in slot 78 so as to detach retaining and retrieval device 74 from the rest of biopsy instrument 75. As shown therein, tissue specimen 85 is held by barbs 82 such that device 74 with tissue specimen 85 affixed thereto can be deposited in a vial of preservative solution for easy retrieval therefrom.

FIG. 21 shows a manufacturing blank 90 for another preferred embodiment of a retaining and retrieval device for a biopsy instrument in accordance with the invention. Similarly, FIG. 22 shows a manufacturing blank 95 for another preferred embodiment of a retaining and retrieval device for a biopsy instrument in accordance with the invention.

Another embodiment of a biopsy instrument 101 in accordance with the invention is illustrated in FIG. 23. The biopsy instrument 101 of FIG. 23 is shown in FIG. 24 entering an area of tissue 107. As seen in FIG. 25, the retaining and retrieval device 102 of the biopsy instrument 101 functions to sever and grasp a tissue specimen 108.

Obviously, numerous modifications and variations of the present invention are possible in the light of the above teachings. For example, other methods of controlling the relative rotation between the specimen retaining and retrieval device and the tissue penetrating device are possible. It is therefore to be understood that, within the scope of the claims appended hereto, the invention may be practiced otherwise than as specifically disclosed herein.

What is claimed is:

1. A biopsy instrument, comprising:

a tissue penetrating device including an elongated holder and a tubular cutting member connected to one end of said holder, said cutting member having a forward cutting edge for penetrating tissue whereupon a tissue portion becomes enclosed within and surrounded by said tubular cutting member; and a specimen retaining and retrieval device detachably connected to said tissue penetrating device on the exterior of said cutting member for separating and retaining a specimen of tissue including said tissue portion enclosed within said cutting member from surrounding tissue and for withdrawing, upon detachment from said tissue penetrating device, said specimen from said tissue penetrating device for subsequent contact with and retrieval from a preservative solution.

2. The biopsy instrument of claim 1, wherein said specimen retaining and retrieval device comprises means for controlling relative rotation between it and said tissue penetrating device.

3. The biopsy instrument of claim 1, wherein said cutting member is open only at one end.

4. A biopsy instrument, comprising:

a tissue penetrating device including an elongated holder and a cutting member connected to one end of said holder and having a cutting edge for penetrating tissue, said cutting edge being shaped so as to enclose substantially a portion of penetrated tissue within said cutting member; and a specimen retaining and retrieval device having a handle, said specimen retaining and retrieval device being detachably connected to said tissue penetrating device for separating and retaining a specimen of tissue including tissue enclosed within said cutting member from surrounding tissue and for withdrawing, upon detachment from said tissue penetrating device, said specimen from said tissue penetrating device, for subsequent contact with and retrieval from a preservation solution; and means for detachably attaching said specimen retaining and retrieval device to said tissue penetrating device, and wherein said attaching means comprises a pin mounted in a recess in an outside surface of said holder of said tissue penetrating device and a pair of guide members aligned in parallel on said outside surface, and said handle comprises a longitudinal slit ending in a large hole, said pin projecting through said slit such that said handle can move axially relative to said holder by axial movement of said slit relative to said pin, said guide members preventing substantial rotational relative movement between said handle and said holder, and wherein movement of said hole in said handle over said pin permits detachment of said specimen retaining and retrieval means from said tissue penetrating device.

5. The biopsy instrument of claim 4, wherein said handle further comprises a tab at one end which limits its forward axial movement by interference of said tab with said guide members.

* * * * *